United States Patent [19]

Tracy et al.

[11] Patent Number: 4,698,412

[45] Date of Patent: Oct. 6, 1987

[54] LACTAM COPOLYMERS

[75] Inventors: David J. Tracy, Lincoln Park; Robert B. Login, Oakland; Mohamed M. Hashem, Wayne, all of N.J.

[73] Assignee: GAF Corporation, Wayne, N.J.

[21] Appl. No.: 20,841

[22] Filed: Mar. 2, 1987

[51] Int. Cl.[4] ............................................. C08G 69/20
[52] U.S. Cl. .................................. 528/323; 528/326; 540/525; 546/188; 548/519
[58] Field of Search ................ 526/323, 326; 548/519; 546/188; 540/525

*Primary Examiner*—Paul R. Michl
*Attorney, Agent, or Firm*—Marilyn J. Maue; Joshua J. Ward

[57] ABSTRACT

Copolymers of propylene oxide and N-epoxy propyl lactams having the structures

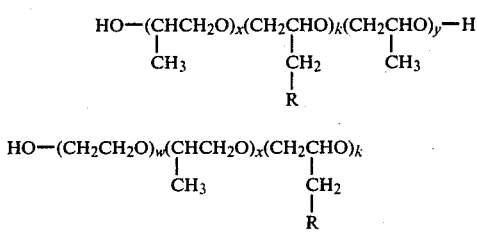

-continued

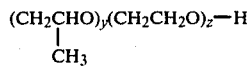

or

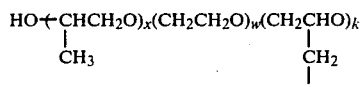

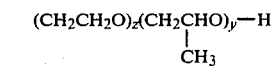

wherein R is

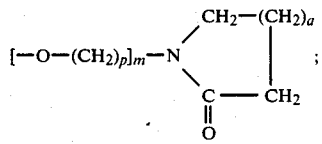

$a$ has a value of 1–3; $p$ has a value of 1–2; $m$ has a value of 0–1; $k$ has a value of 2–200; $w$ and $z$ each have a value of 2–50 $x$ and $y$ have a value of 2–100; and also the process for preparing the aforementioned copolymers as well as their use as surfactants.

10 Claims, No Drawings

LACTAM COPOLYMERS

According to this invention there is provided a copolymer of propylene oxide and a pyrrolidone having the formula

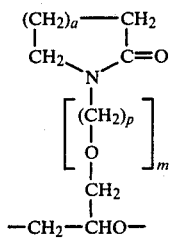

wherein a has a value of 1–3; p has a value of 1–2 and m has a value of 0–1; said copolymer containing from 2 to 200 units of said pyrrolidone; from 2 to 100 propyleneoxy units, referred to herein as PO units, and from 0 to 50 ethyleneoxy units, referred to herein as EO units, said propyleneoxy units representing the predominant alkyleneoxy content of the copolymer. Specific examples of the present copolymers include the following which may occur in random or in block structure arrangement

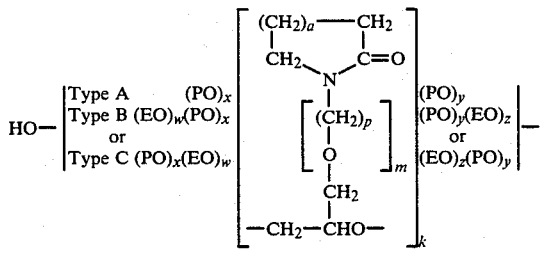

wherein subscripts have the following values:

| | |
|---|---|
| a = 1–3 | w = 2–50 |
| k = 2–200 | x = 2–100 |
| m = 0–1 | y = 2–100 |
| p = 1–2 | z = 2–50; | the sum of x and y is between 4 and 150 and PO is the major alkyleneoxy unit of the copolymer. Of the above copolymers, those wherein a has a value of one, the sum of x and y is between 15 and 50 and k has a value between 8 and 25, are preferred.

The present copolymers are prepared by a commercially economical process. More particularly the pyrrolidone/propyleneoxide copolymers of Type A can be prepared by reacting the corresponding pyrrolidone homopolymer, i.e.

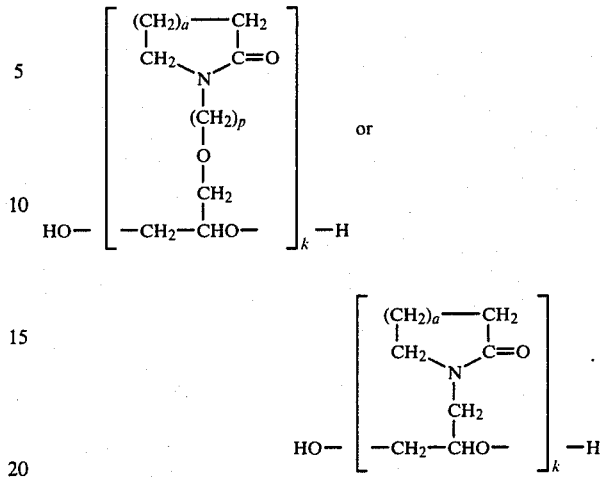

with propylene oxide in the presence of an inorganic hydroxide at a temperature of between about 100° C. and about 150° C. under from about 14 to about 50 psig for a period of from about 0.5 to about 15 hours.

The pyrrolidone/propylene oxide/ethylene oxide polymers of Type B can be prepared by reacting the product of Type A with a molar excess of ethylene oxide, preferably a molar excess of between about 8 and about 20 moles, at a somewhat higher temperature, e.g. 115°–180° C., under a pressure ranging from atmospheric to about 50 psig for a period of from about 0.5 to about 15 hours.

The preparation of copolymers of Type C can be effected by the procedure described for Type A, except that ethylene oxide is substituted for propylene oxide and the product of this reaction is contacted with propylene oxide under the conditions set forth in the reaction of ethylene oxide with the product of Type A.

The products of these reactions are recovered by neutralizing the product solutions, cooling to room temperature, washing the solid product with water and drying.

The above processes tend to provide polymers of block structure. To obtain polymers of more random distribution, all of the monomers of the various components are mixed and reacted under the conditions disclosed for Type B.

The polymers of this invention are useful as high efficiency surfactants and complexing agents and can be incorporated in amounts between about 0.01 wt. % and about 20 wt. % in various compositions including detergent, medicinal and cosmetic formulations. The products of this invention find particular application in standard shampoo, cosmetic cream and lotion formulatins wherein the copolymer provides moisturizing effects.

Having broadly described the invention, reference is now made to the following examples which describe preferred embodiments but which are not to be construed as limiting to the scope of the invention as more broadly set forth above and in the appended claims.

EXAMPLE 1

Preparation of

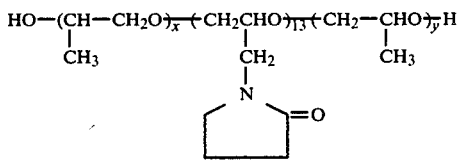

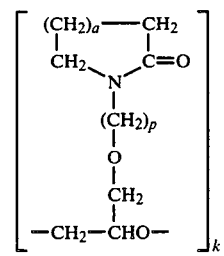

wherein the sum of x and y is 30.

N-Epoxypropyl pyrrolidone homopolymer having a number average molecular weight of 1900 is prepared by the method of F. P. Sidelkorskaya (Vysokomol. Soedin Ser. B, 10(3), 187–189, 1968). To 1900 g. or 1 mole of the homopolymer is added 0.1 wt. % of potassium hydroxide and 30 moles of propylene oxide at a temperature of 110°–125° C. under 50 to 75 psig. After all propylene oxide is reacted or taken up (about 7 hours) the resulting copolymer is cooled, neutralized with phosphoric acid and recovered by drying.

EXAMPLE 2

Preparation of

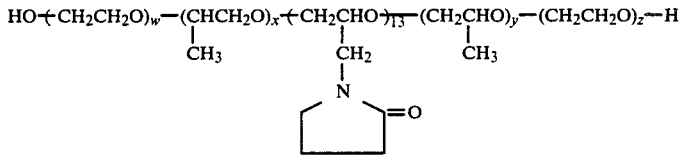

wherein the sum of x and y is 30 and the sum of w and z is 10. About 10 moles of ethylene oxide per mole of unneutralized product obtained in Example 1 is added to an autoclave and heated at 160° C. under 20 psig. pressure for 7 hours; after which the resulting product is cooled, neutralized, and dried.

EXAMPLE 3

Preparation of

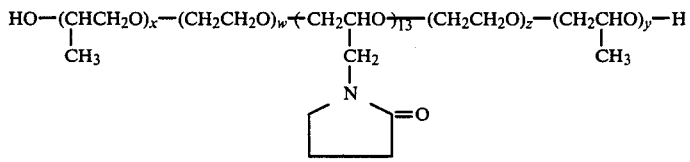

wherein the sum of w and z is 10 and the sum of x and y is 25.

Example 1 is repeated except that about 10 moles of ethylene oxide is substituted for 30 moles of propylene oxide, after which the process of Example 2 is repeated except that 30 moles of propylene oxide is substituted for 10 moles of ethylene oxide therein.

Many modifications and variations of the above examples will become apparent from the foregoing disclosure. For example the homopolymers e.g. prepared by the process disclosed in co-pending patent application, Ser. No. 021,053 filed on Mar. 2, 1987, entitled EPOXY PYRROLIDONE BASED NON-IONIC SURFACTANTS, filed concurrently herewith, can be substituted in any of the preceding examples to produce the corresponding polymer having excellent surfactant and complexing properties.

What is claimed is:

1. A hydroxy terminated lactam/alkyleneoxide copolymer consisting essentially of:

(a) from 2 to 200 units of a lactam monomer having the structure

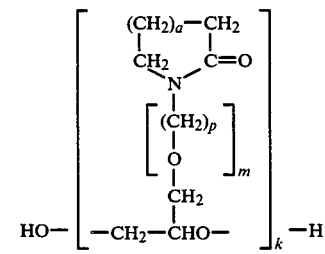

wherein a has a value of 1–3, p has a value of 1–2 and m has a value of 0–1;

(b) from 2 to 100 units of propylene oxide and (c) from 0 to 50 units of ethylene oxide said polymer containing a major amount of the propylene oxide units with respect to ethylene oxide units.

2. The copolymer of claim 1 wherein the mole ratio of said propylene oxide units to units of said lactam monomer is between about 1.5:1 and about 5:1.

3. The copolymer of claim 1 wherein said lactam monomer is a pyrrolidinonyl unit selected from the group of

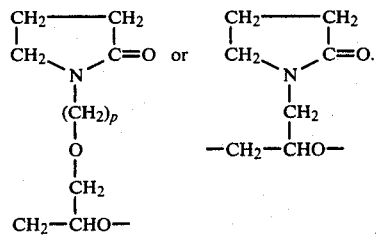
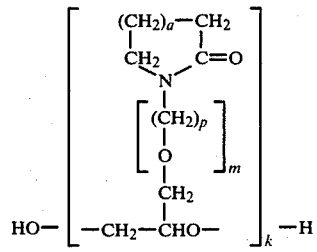

4. The copolymer of claim 3 having a structure selected from the group of

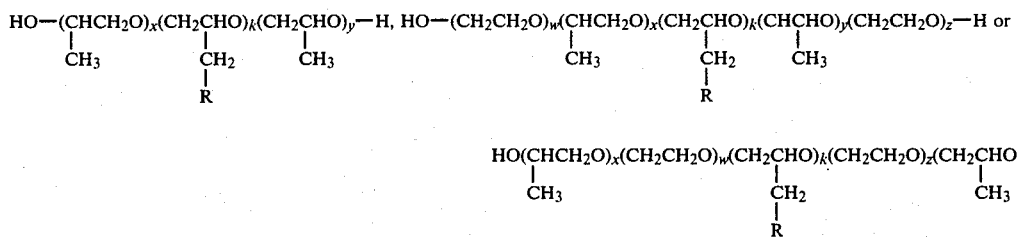

wherein R is selected from the group of

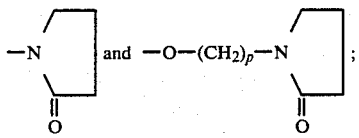

K has a value of 6–50; p has a value of 1–2; w and z each have a value of 2–50 and x and y each have a value of 2–100.

5. The process of adding an effective surfactant amount of the copolymer of claim 1 to a water insoluble liquid.

6. The process of adding an effective complexing amount of the copolymer of claim 1 to a water insoluble medicinal compound.

7. The process of adding an effective surfactant amount of the copolymer of claim 1 to a cosmetic formulation.

8. The process for producing a copolymer of claim 1 which comprises reacting a homopolymer of an epoxypropyl pyrrolidone having the structure with a molar excess of propylene oxide in the presence of an inorganic hydroxide at a temperature of between about 100° C. and about 150° C. under from about 14 to about 50 psig. to produce the copolymer product having the structure

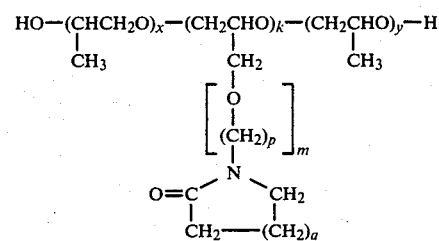

wherein a, m and p, have the values assigned in claim 1; x and y each have a value of from 2 to 100 and k has a value of 2–200.

9. The process for producing the copolymer having the structure

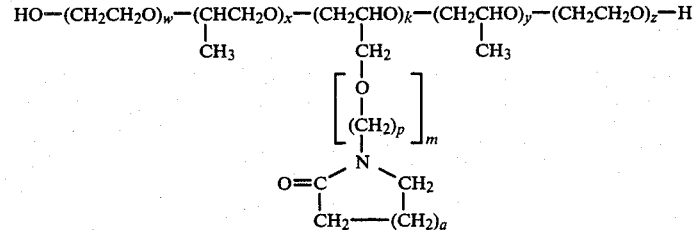

wherein a, k, m, p, x and y have the values assigned in claim 8 and each of w and z have a value of 2–50 which comprises reacting the copolymer product of claim 8 with ethylene oxide in a mole ratio of between about 0.1 and about 0.5 with respect to the propylene oxide content, at a temperature of between about 115° C. and about 180° C. under atmospheric to about 50 psig. pressure.

10. The process for producing the copolymer having the structure

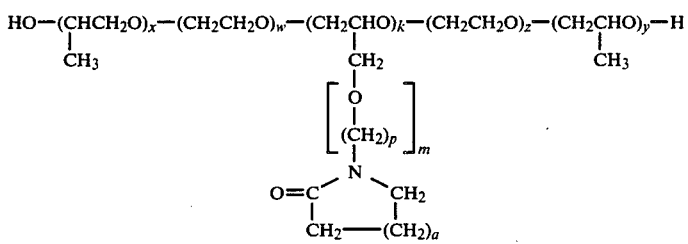

which comprises reacting a homopolymer of an epoxypropyl pyrrolidone having the structure

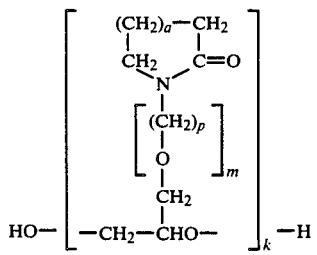

wherein a, k, m, p, x, y, w and z have the values assigned in claim 9, with ethylene oxide in the presence of an inorganic hydroxide at a temperature of between about 100° C. and about 150° C. under a pressure of from about 14 to about 50 psig. until the copolymeric product of the epoxypropyl pyrrolidone and ethylene oxide is produced and reacting said copolymeric product with a molar excess of propylene oxide, based on the amount of ethylene oxide in the copolymer product, at a temperature of between about 100° C. and about 180° C. under from atmosphereic to about 50 psig. pressure.

* * * * *